(12) United States Patent
Schlom et al.

(10) Patent No.: US 8,748,390 B2
(45) Date of Patent: Jun. 10, 2014

(54) IMMUNOGENIC EPITOPES OF NGEP ANTIGEN

(75) Inventors: Jeffrey Schlom, Potomac, MD (US); Kwong-Yok Tsang, Bethesda, MD (US); Ira Pastan, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/265,490

(22) PCT Filed: Apr. 19, 2010

(86) PCT No.: PCT/US2010/031584
§ 371 (c)(1),
(2), (4) Date: Nov. 9, 2011

(87) PCT Pub. No.: WO2010/123813
PCT Pub. Date: Oct. 28, 2010

(65) Prior Publication Data
US 2012/0052116 A1 Mar. 1, 2012

Related U.S. Application Data

(60) Provisional application No. 61/170,900, filed on Apr. 20, 2009.

(51) Int. Cl.
*A61K 38/08* (2006.01)
*A61K 39/00* (2006.01)
*C07K 7/06* (2006.01)

(52) U.S. Cl.
USPC ....... 514/19.3; 424/277.1; 514/21.6; 530/328

(58) Field of Classification Search
None
See application file for complete search history.

(56) References Cited

U.S. PATENT DOCUMENTS 5,846,827 A * 12/1998 Celis et al. .................... 435/384
2004/0241702 A1 12/2004 Pastan et al.
2006/0194204 A1 8/2006 Pastan et al.

FOREIGN PATENT DOCUMENTS

| WO | WO 03/042370 A2 | 5/2003 |
| WO | WO 2004/092213 A1 | 10/2004 |
| WO | WO 2005/007830 A2 | 1/2005 |
| WO | WO 2006/110593 A2 | 10/2006 |

OTHER PUBLICATIONS

Oxenius, Journal of Virology, vol. 73, No. 5, p. 4120-4126, 1999.*
Heffernan, Biomaterials, vol. 32, p. 926-932, 2011.*
International Preliminary Report on Patentability from the International Bureau of WIPO, issued in PCT/US2010/031584, mailed Nov. 3, 2011, 8 pages.
Arlen et al., "A randomized phase II study of concurrent docetaxel plus vaccine versus vaccine alone in metastatic androgen-independent prostate cancer," *Clin. Cancer Res.*, 12 (4), 1260-1269 (2006).
Arlen et al., "Strategies for the development of PSA-based vaccines for the treatment of advanced prostate cancer," *Expert Rev. Vaccines*, 2 (4), 483-493 (2003).
Bera et al., "NGEP, a gene encoding a membrane protein detected only in prostate cancer and normal prostate," *Proc. Natl. Acad. Sci. USA*, 101 (9), 3059-3064 (2004).
Carter et al., "Prostate-specific membrane antigen is a hydrolase with substrate and pharmacologic characteristics of a neuropeptidase," *Proc. Natl. Acad. Sci. USA*, 93 (2), 749-753 (1996).
Cereda et al., "New gene expressed in prostate: a potential target for T cell-mediated prostate cancer immunotherapy," *Cancer Immunol. Immunother.*, 59 (1), 63-71 (2010).
Das et al., "Topology of NGEP, a prostate-specific cell:cell junction protein widely expressed in many cancers of different grade level," *Cancer Res.*, 68 (15), 6306-6312 (2008).
Das et al., "NGEP, a prostate-specific plasma membrane protein that promotes the association of LNCaP cells," *Cancer Res*, 67 (4), 1594-1601 (2007).
Ghosh et al., "Tumor target prostate specific membrane antigen (PSMA) and its regulation in prostate cancer," *J. Cell Biochem.*, 91 (3), 528-539 (2004).
Gulley et al., "Combining a recombinant cancer vaccine with standard definitive radiotherapy in patients with localized prostate cancer," *Clin. Cancer Res.*, 11 (9), 3353-3362 (2005).
Harada et al., "Target molecules in specific immunotherapy against prostate cancer," *Int. J. Clin. Oncol.*, 8 (4), 193-199 (2003).
Iavarone et al., "PAGE4 is a cytoplasmic protein that is expressed in normal prostate and in prostate cancers," *Mol. Cancer Ther.*, 1 (5), 329-335 (2002).
International Search Report, Application No. PCT/US2010/031584, dated Jun. 28, 2010.
Jalkut et al., "Role of prostate stem cell antigen in prostate cancer research," *Curr. Opin. Urol.*, 12 (5), 401-406 (2002).
Jemal et al., "Cancer statistics, 2008," *CA Cancer J. Clin.*, 58 (2), 71-96 (2008).
Karnes et al., "Immunotherapy for prostate cancer," *Curr. Pharm. Des.*, 12 (7), 807-817 (2006).
Katoh et al., "Characterization of human TMEM16G gene in silico," *Int. J. Mol. Med.*, 14 (4), 759-764 (2004).
Kiessling et al., "Prostate stem cell antigen: Identification of immunogenic peptides and assessment of reactive CD8+ T cells in prostate cancer patients," *Int. J. Cancer*, 102 (4), 390-397 (2002).
Kiessling et al., "D-TMPP: a novel androgen-regulated gene preferentially expressed in prostate and prostate cancer that is the first characterized member of an eukaryotic gene family," *Prostate*, 64 (4), 387-400 (2005).

(Continued)

*Primary Examiner* — Misook Yu
*Assistant Examiner* — Michael D Allen
(74) *Attorney, Agent, or Firm* — Leydig, Voit & Mayer, Ltd.

(57) ABSTRACT

The invention provides a peptide comprising a human cytolytic T lymphocyte (CTL) epitope from the human tumor-associated antigen (TAA) New Gene Expressed in Prostate (NGEP), which can be used in vaccine prevention or therapy of prostate cancer, as well as a nucleic acid encoding the peptide, a vector comprising the nucleic acid, a cell comprising the peptide, nucleic acid, or vector, and compositions thereof.

24 Claims, 4 Drawing Sheets

(56) References Cited

OTHER PUBLICATIONS

Figure 1A:
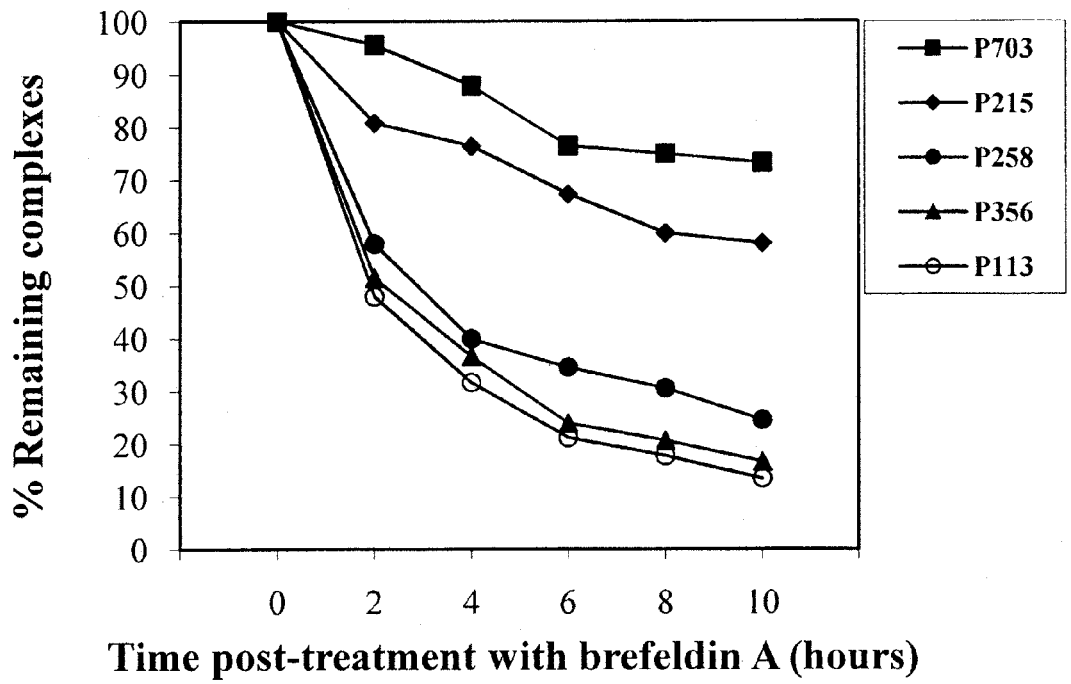

Lilja et al., "Prostate-specific antigen and prostate cancer: prediction, detection and monitoring," *Nat. Rev. Cancer*, 8 (4), 268-278 (2008).

Parker et al., "Scheme for ranking potential HLA-A2 binding peptides based on independent binding of individual peptide sidechains," *J. Immunol.*, 152 (1), 163-175 (1994).

Peshwa et al., "Induction of prostate tumor-specific CD8+ cytotoxic T-lymphocytes in vitro using antigen-presenting cells pulsed with prostatic acid phosphatase peptide," *Prostate*, 36 (2), 129-138 (1998).

Reiter et al., "Prostate stem cell antigen: a cell surface marker overexpressed in prostate cancer," *Proc. Natl. Acad. Sci. USA*, 95 (4), 1735-1740 (1998).

Schlom et al., "Role of vaccine therapy in cancer: biology and practice," *Curr. Oncol.*, 14 (6), 238-245 (2007).

Slovin et al., "Targeting novel antigens for prostate cancer treatment: focus on prostate-specific membrane antigen," *Expert Opin. Ther. Targets*, 9 (3), 561-570 (2005).

Taira et al., "Reviving the acid phosphatase test for prostate cancer," *Oncology* (*Williston Park* ), 21 (8), 1003-1010 (2007).

Written Opinion of the International Searching Authority, Application No. PCT/US2010/031584, dated Jun. 28, 2010.

Yokokawa et al., "Identification of cytotoxic T-lymphocyte epitope(s) and its agonist epitope(s) of a novel target for vaccine therapy (PAGE4)," *Int. J. Cancer*, 121 (3), 595-605 (2007).

* cited by examiner

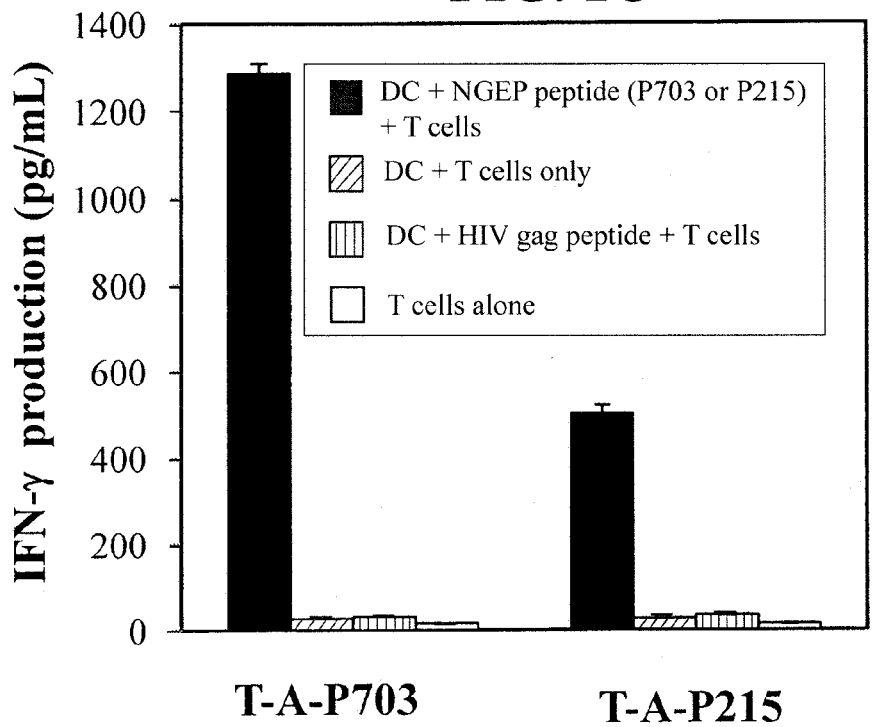
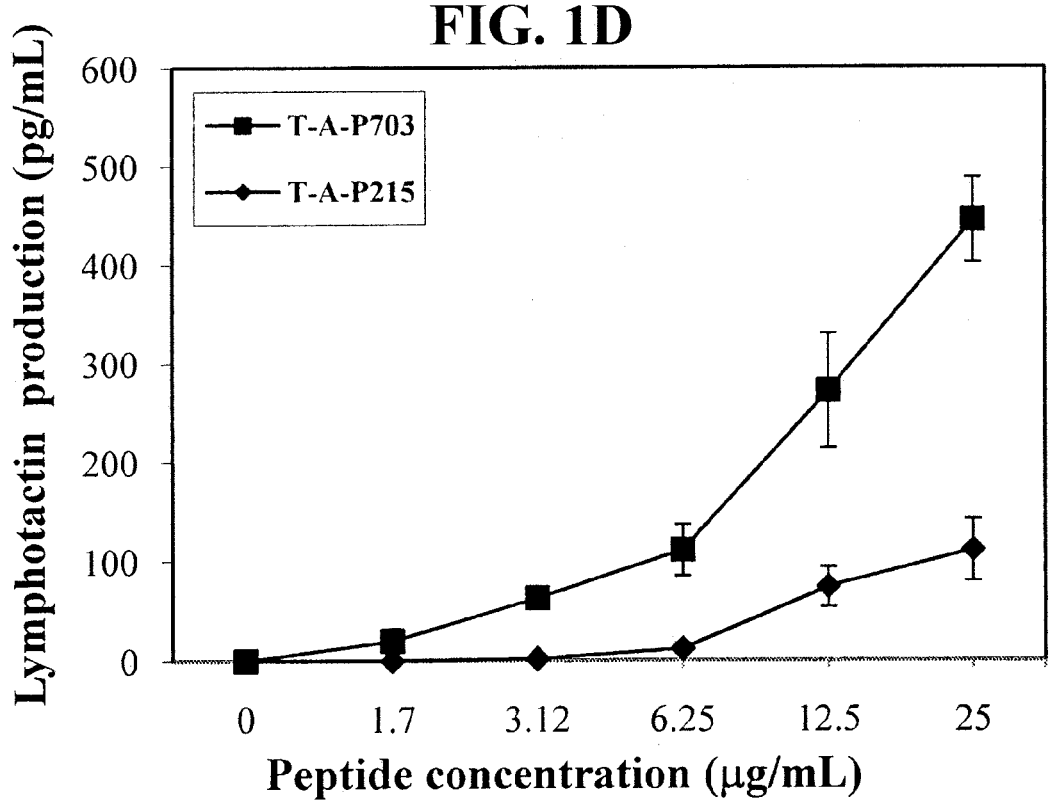

T-A-P703

T-A-P703

US 8,748,390 B2

IMMUNOGENIC EPITOPES OF NGEP ANTIGEN

CROSS-REFERENCE TO RELATED APPLICATIONS

This patent application is a U.S. National Phase of International Patent Application No. PCT/US10/31584, filed Apr. 19, 2010, which claims the benefit of U.S. Provisional Patent Application No. 61/170,900, filed Apr. 20, 2009, which are incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 3,091 Byte ASCII (Text) file named "708862_ST25.txt," created on Sep. 7, 2011.

BACKGROUND OF THE INVENTION

Prostate cancer is one of the most common cancers in men in the United States, with 186,320 new cases estimated in 2008 and one of the leading causes of cancer death among males with approximately 28,660 deaths estimated in 2008 (see, e.g., Jemal et al., *CA Cancer J. Clin.*, 58: 71-96 (2008)). Despite recent advances in androgen-deprivation therapy and chemotherapy, there is currently no curative treatment for metastatic prostate cancer. Current therapies are unable to completely eliminate androgen-independent prostate cancer cells that remain after androgen ablation (see, e.g., Karnes et al., *Curr. Pharm. Des.*, 12: 807-817 (2006)).

One approach to prostate cancer treatment is specific immunotherapy, either alone or in combination with standard definitive radiation therapy or chemotherapy (see, e.g., Arlen et al., *Clin. Cancer Res.*, 12: 1260-1269 (2006); and Gulley et al., *Clin. Cancer Res.*, 11: 3353-3362 (2005)). In the last few years, immunotherapy employing several different prostate cancer vaccines has shown promising evidence of clinical benefit in various patient populations (see, e.g., Schlom et al., *Curr. Oncol.*, 14: 238-245 (2007); and Harada et al., *Int. J. Clin. Oncol.*, 8: 193-199 (2003)). Tissue-specific antigens, which are expressed in both normal prostate and prostate cancer cells, can be targeted for prostate cancer-specific immunotherapy. Prostate cancer-associated antigens have been identified (see, e.g., Arlen et al., *Expert Rev. Vaccines*, 2: 483-493 (2003); Ghosh et al., *J. Cell Biochem.*, 91: 528-539 (2004); Iavarone et al., *Mol. Cancer. Ther.*, 1: 329-335 (2002); Jalkut et al., *Curr Opin. Urol.*, 12: 401-406 (2002); Kiessling et al., *Int. J. Cancer*, 102: 390-397 (2002); Likja et al., *Nat. Rev. Cancer*, 8: 268-278 (2008); Peshwa et al., *Prostate*, 36: 129-138 (1998); Slovin et al., *Expert Opin. Ther. Targets*, 9: 561-570 (2005); Taira et al., *Oncology (Williston Park)*, 21: 1003-1010 (2007); and Yokokawa et al., *Int. J. Cancer*, 121: 595-605 (2007)). Several of these antigens, however, also are expressed in some normal tissues (see, e.g., Carter et al., *Proc. Natl. Acad. Sci. USA*, 93: 749-753 (1996); and Reiter et al., *Proc. Natl. Acad. Sci. USA*, 95: 1735-1740 (1998)).

Therefore, the desire exists for new approaches for the treatment of prostate cancer.

BRIEF SUMMARY OF THE INVENTION

The invention provides a peptide having no more than 20 amino acids that comprises GLFDEYLEMV (SEQ ID NO: 1), LVWEEDLKL (SEQ ID NO: 2), WLLPAAVVGT (SEQ ID NO: 3), GLGGPPLPTL (SEQ ID NO: 4), IVFEHVVFSV (SEQ ID NO: 5), or FLDNIRAAGL (SEQ ID NO: 6). In another aspect, the invention provides a nucleic acid encoding the peptide, a vector comprising the nucleic acid, a cell comprising the peptide, nucleic acid, or vector, and compositions thereof.

The invention also provides a method of enhancing an immune response against prostate cancer in a host comprising administering a therapeutically effective amount of a composition comprising the peptide, nucleic acid, vector, or cell to the host, wherein the immune response in the host is enhanced.

The invention further provides a method of inhibiting prostate cancer in a host comprising (a) stimulating lymphocytes with the peptide, nucleic acid, vector, cell, or composition thereof to generate cytotoxic T lymphocytes, and (b) administering the cytotoxic T lymphocytes to the host, wherein prostate cancer is inhibited.

BRIEF DESCRIPTION OF THE SEVERAL VIEWS OF THE DRAWING(S)

FIG. 1A is a graph depicting the stability of HLA-A2/NGEP complexes for various peptides. The time post-treatment with brefeldin A (hours) is on the x-axis, and the percentage of remaining complexes is on the y-axis. Results are expressed in relative percentage of binding compared to 100% at time 0.

Figure 1B:
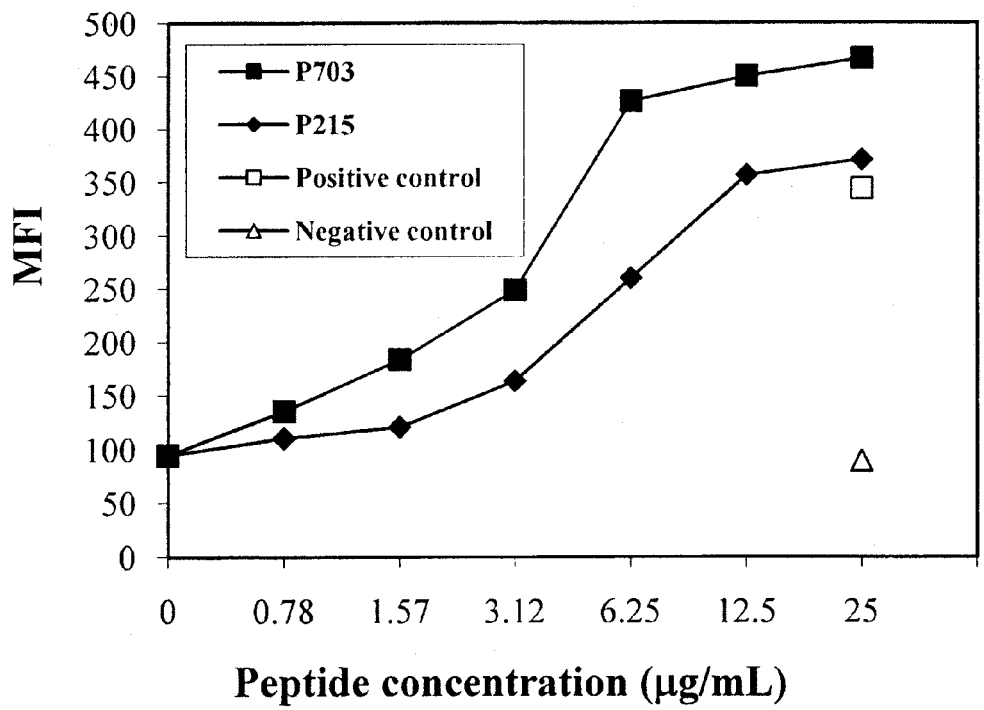

FIG. 1B is a graph depicting the binding of the P703 and P215 peptides to HLA-A2 molecules at various peptide concentrations. Peptide concentration (μg/mL) is on the x-axis, and mean fluorescence intensity (MFI) is on the y-axis. The positive control peptide is MUC-1, and the negative control peptide is CAP-7.

FIG. 1C is a graph depicting interferon (IFN)-γ production by NGEP-specific T-cell lines. The results are expressed in pg/mL. Standard deviation is indicated by the bars.

FIG. 1D is a graph depicting the lymphotactin production by the NGEP-specific T-cell lines, T-A-P703 and T-A-P215, at various peptide concentrations. Peptide concentration (μg/mL) is on the x-axis, and lymphotactin production (pg/mL) is on the y-axis. Standard deviation is indicated by the bars.

Figure 2A:
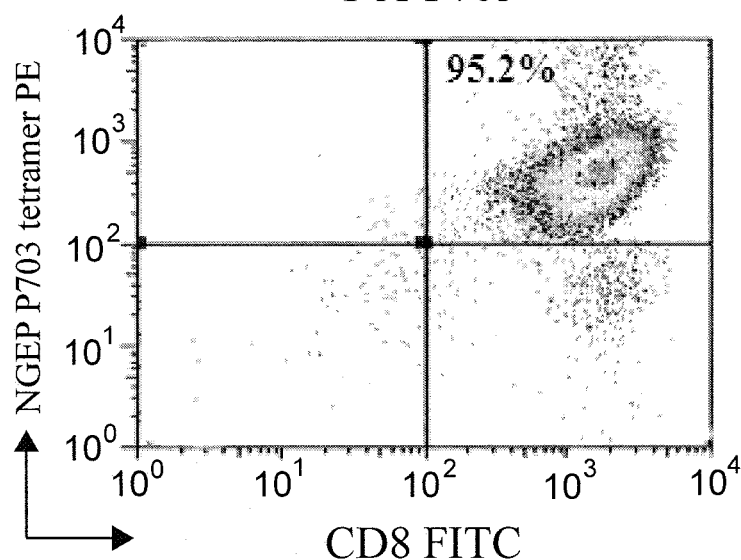

FIG. 2A is a graph depicting the frequency of NGEP-specific CD8$^+$ T cells in the T-A-P703 cell line (generated using peptide P703) by staining T cells with PE-labeled NGEP-P703/HLA-A*0201 tetramer and anti-CD8 antibody ($1 \times 10^6$ cells/20 μL) at IVS-3. The percentage indicated is the percentage of tetramer positive NGEP-specific T cells in the CD8$^+$ T cell population.

Figure 2B:
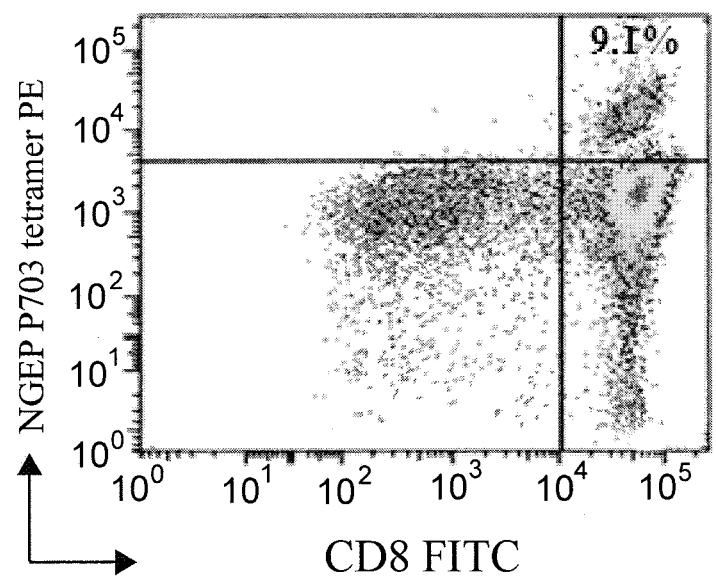

FIG. 2B is a graph depicting the frequency of NGEP-specific CD8$^+$ T cells in the T-B-P703 cell line (an additional cell line generated using peptide P703) by staining T cells with PE-labeled NGEP-P703/HLA-A*0201 tetramer and anti-CD8 antibody ($1 \times 10^6$ cells/20 μL) at IVS-3. The percentage indicated is the percentage of tetramer positive NGEP-specific T cells in the CD8$^+$ T cell population.

Figure 2C:
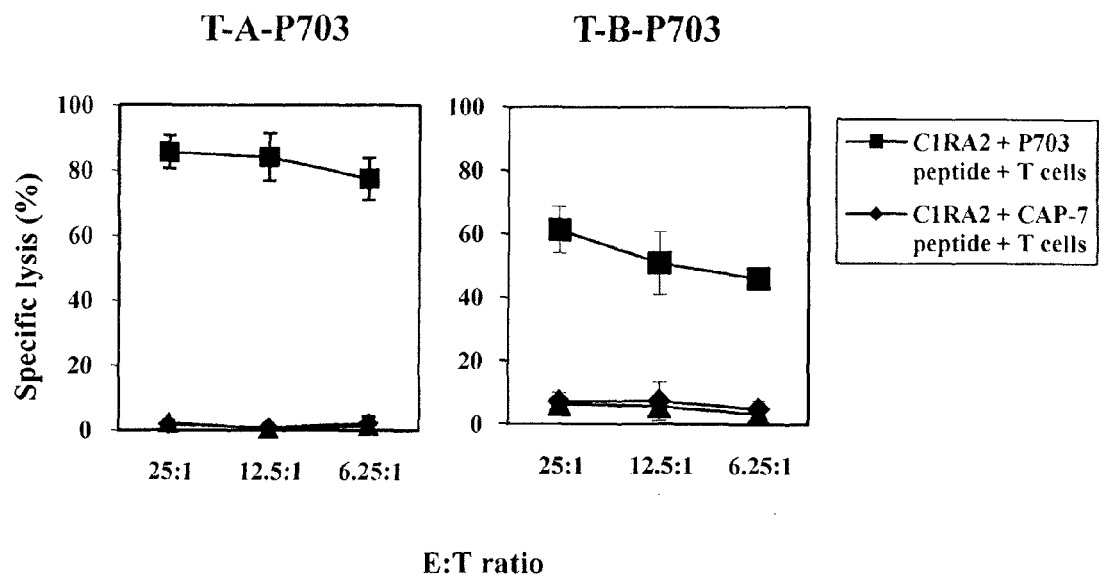

FIG. 2C is a graph depicting the cytotoxic activity of the T-A-P703 and T-B-P703 cell lines on CIRA-2 pulsed with NGEP or control peptide (CAP-7). The effector:target (E:T) ratio is indicated on the x-axis and the percentage of specific lysis is indicated on the y-axis. Standard deviation is indicated by the bars.

Figure 2D:
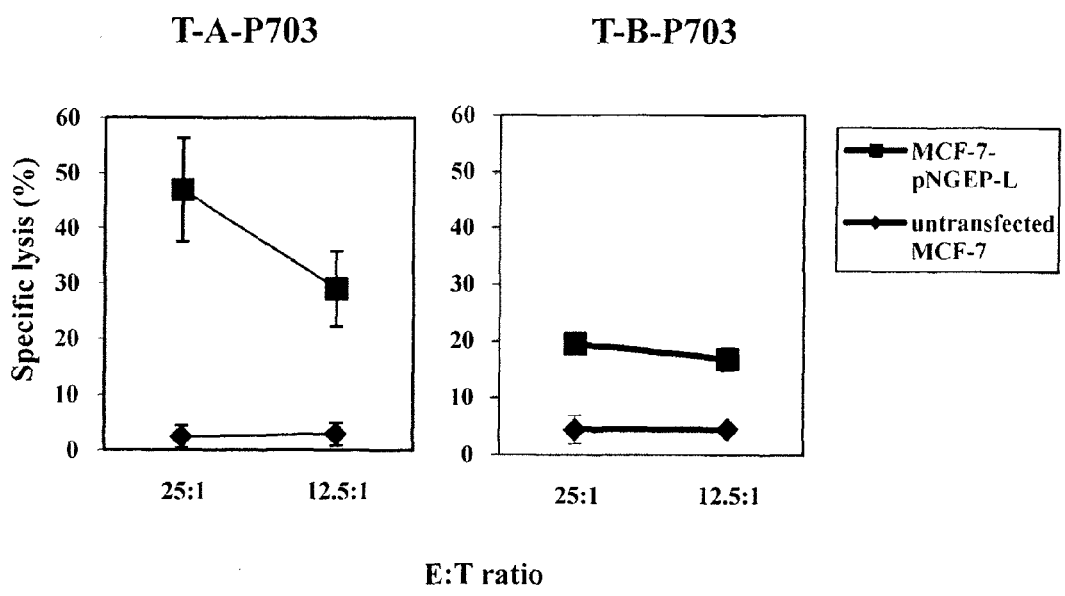

FIG. 2D is a graph depicting cytotoxic activity of the T-A-P703 and T-B-P703 cell lines on MCF-7 cells transfected with the NGEP gene (MCF7-pNGEP-L). Untransfected MCF-7 cells were used as a control. The E:T ratio is indicated on the x-axis, and the percentage of specific lysis is indicated on the y-axis. Standard deviation is indicated by the bars.

DETAILED DESCRIPTION OF THE INVENTION

The invention provides a peptide comprising a human cytolytic T lymphocyte (CTL) epitope from the human tumor-associated antigen (TAA) New Gene Expressed in Prostate (NGEP), which can be used in vaccine prevention or therapy of prostate cancer.

The NGEP gene, also known as TMEM16G, is located on chromosome 2 at 2q37.3. There are two spliced forms of NGEP mRNA. The smaller transcript (NGEP-S) encodes a 179-amino acid cytoplasmic protein, and the larger transcript (NGEP-L) encodes a 933-amino acid polytopic membrane protein that is a member of the TMEM16 protein family (see, e.g., Bera et al., *Proc. Natl. Acad. Sci. USA,* 101: 3059-3064 (2004)). NGEP-L is present in prostate tissue samples (normal, benign prostatic hyperplasia, and prostate cancer), but not in other tumors or essential normal tissues (see, e.g., Bera et al., supra, Das et al., *Cancer Res,* 67: 1594-1601 (2007); and Das et al., *Cancer Res.,* 68: 6306-6312 (2008)).

The inventive peptide has no more than 20 (e.g., no more than 19, no more than 18, no more than 17, no more than 16, no more than 15, no more than 14, no more than 13, no more than 12, no more than 11, or no more than 10) amino acid residues and comprises the amino acid sequence of GLFDEYLEMV (SEQ ID NO: 1). Alternatively, the inventive peptide has no more than 20 (e.g., no more than 19, no more than 18, no more than 17, no more than 16, no more than 15, no more than 14, no more than 13, no more than 12, no more than 11, or no more than 10) amino acid residues and comprises an amino acid sequence selected from the group consisting of LVWEEDLKL (SEQ ID NO: 2), WLLPAAV-VGT (SEQ ID NO: 3), GLGGPPLPTL (SEQ ID NO: 4), IVFEHVVFSV (SEQ ID NO: 5), or FLDNIRAAGL (SEQ ID NO: 6).

In one embodiment, the inventive peptide consists of the amino acid sequence of SEQ ID NO: 1. In another embodiment, the inventive peptide consists of an amino acid sequence selected from the group consisting of SEQ ID NO: 2, SEQ ID NO: 3, SEQ ID NO: 4, SEQ ID NO: 5, or SEQ ID NO: 6.

The inventive peptide can be a fragment of the NGEP (NGEP-S or NGEP-L) protein that comprises no more than 20 contiguous amino acids of the NGEP (NGEP-S or NGEP-L) protein, wherein the peptide comprises the amino acid sequence of SEQ ID NO: 1, SEQ ID NO: 2, SEQ ID NO: 3, SEQ ID NO: 4, SEQ ID NO: 5, or SEQ ID NO: 6. The additional amino acid residues of the NGEP protein can be positioned at either end or both ends of the amino acid sequence of SEQ ID NO: 1, SEQ ID NO: 2, SEQ ID NO: 3, SEQ ID NO: 4, SEQ ID NO: 5, or SEQ ID NO: 6.

The inventive peptide can comprise no more than 11 (e.g., no more than 10, no more than 9, no more than 8, no more than 7, no more than 6, no more than 5, no more than 4, no more than 3, no more than 2, no more than 1, or 0) amino acid residues at the C terminus of the amino acid sequence of SEQ ID NO: 1, SEQ ID NO: 2, SEQ ID NO: 3, SEQ ID NO: 4, SEQ ID NO: 5, or SEQ ID NO: 6, and/or no more than 11 (e.g., no more than 10, no more than 9, no more than 8, no more than 7, no more than 6, no more than 5, no more than 4, no more than 3, no more than 2, no more than 1, or 0) amino acid residues at the N terminus of the amino acid sequence of SEQ ID NO: 1, SEQ ID NO: 2, SEQ ID NO: 3, SEQ ID NO: 4, SEQ ID NO: 5, or SEQ ID NO: 6, wherein the inventive peptide has no more than 20 amino acid residues in total.

The peptide can be prepared by any method, such as by synthesizing the peptide or by expressing a nucleic acid encoding an appropriate amino acid sequence in a cell and harvesting the peptide from the cell. A combination of such methods also can be used. Methods of de novo synthesizing peptides and methods of recombinantly producing peptides are known in the art (see, e.g., Chan et al., *Fmoc Solid Phase Peptide Synthesis,* Oxford University Press, Oxford, United Kingdom, 2005; *Peptide and Protein Drug Analysis,* ed. Reid, R., Marcel Dekker, Inc., 2000; *Epitope Mapping,* ed. Westwood et al., Oxford University Press, Oxford, United Kingdom, 2000; Sambrook et al., *Molecular Cloning: A Laboratory Manual,* 3$^{rd}$ ed., Cold Spring Harbor Press, Cold Spring Harbor, N.Y. 2001; and Ausubel et al., *Current Protocols in Molecular Biology,* Greene Publishing Associates and John Wiley & Sons, NY, 1994).

The invention also provides a nucleic acid encoding the peptide. The nucleic acid can comprise DNA or RNA, and can be single or double stranded. Furthermore, the nucleic acid can comprise nucleotide analogues or derivatives (e.g., inosine or phosphorothioate nucleotides and the like). The nucleic acid can encode the peptide alone or as part of a fusion protein. The nucleic acid encoding the peptide can be provided as part of a construct comprising the nucleic acid and elements that enable delivery of the nucleic acid to a cell, and/or expression of the nucleic acid in a cell. Such elements include, for example, expression vectors, promoters, and transcription and/or translation sequences. Suitable vectors, promoters, transcription/translation sequences, and other elements, as well as methods of preparing such nucleic acids and constructs, are known in the art (e.g., Sambrook et al., supra; and Ausubel et al., supra).

The invention further provides a vector comprising the nucleic acid. Examples of suitable vectors include plasmids (e.g., DNA plasmids), yeast (e.g., *Saccharomyces*), and viral vectors, such as poxvirus, retrovirus, adenovirus, herpes virus, polio virus, alphavirus, baculorvirus, and Sindbis virus. When the vector is a plasmid (e.g., DNA plasmid), the plasmid can be complexed with chitosan. Preferably, the vector is a poxvirus selected from the group consisting of orthopox, avipox, fowlpox, raccoon pox, rabbit pox, capripox (e.g., sheep pox), leporipox, and suipox (e.g., swinepox). Preferred examples of avipox viruses include fowlpox, pigeonpox, and canarypox, such as ALVAC. Preferred examples of orthopox viruses include vaccinia, modified vaccinia Ankara (MVA), Wyeth, NYVAC, TROYVAC, Dry-Vax, PDXVAC-TC (Schering-Plough Corporation), and derivatives thereof. For example, derivatives of the Wyeth strain include, but are not limited to, derivatives which lack a functional K1L gene.

When the vector is for administration to a host (e.g., human), the vector (e.g., poxvirus) preferably has a low replicative efficiency in a target cell (e.g., no more than about 1 progeny per cell or, more preferably, no more than 0.1 progeny per cell are produced). Replication efficiency can readily be determined empirically by determining the virus titer after infection of the target cell.

In addition to the nucleic acid encoding the peptide, the vector also can comprise gene(s) encoding one or more immunostimulatory/regulatory molecules, granulocyte macrophage colony stimulating factor (GM-CSF), cytokines, or other molecules that can enhance an immune response (e.g., additional tumor-associated antigens, such as prostate specific antigen (PSA)). The nucleic acid encoding the peptide, as well as any other exogenous gene(s), preferably are inserted into a site or region (insertion region) in the vector (e.g., poxvirus) that does not affect virus viability of the resultant recombinant virus. Such regions can be readily identified by testing segments of virus DNA for regions that allow recombinant formation without seriously affecting virus viability of the recombinant virus.

The thymidine kinase (TK) gene is an insertion region that can readily be used and is present in many viruses. In particular, the TK gene has been found in all examined poxvirus genomes. Additional suitable insertion sites are described in International Patent Application Publication WO 2005/048957. For example, in fowlpox, insertion regions include, but are not limited to the BamHI J fragment, EcoRI-HindIII fragment, BamHI fragment, EcoRV-HindIII fragment, long unique sequence (LUS) insertion sites (e.g., FPV006/FPV007 and FPV254/FPV255), FP14 insertion site (FPV060/FPV061), and 43K insertion site (FPV107/FPV108). In vaccinia, insertion sites include, but are not limited to, 44/45, 49/50, and 124/125.

When the vector is a recombinant fowlpox virus comprising a nucleic acid encoding the peptide and/or other exogenous gene(s) (e.g., encoding one or more immunostimulatory/regulatory molecules), the nucleic acid encoding the peptide can be inserted in one region (e.g., the FP14 region), and the exogenous gene(s) can be inserted in another region (e.g., the BamHI J region).

The inventive vector can include suitable promoters and regulatory elements, such as a transcriptional regulatory element or an enhancer. When the vector is a poxvirus vector, poxvirus promoters can be used, including but not limited to the vaccinia 7.5K promoter, vaccinia 30K promoter, vaccinia 40K promoter, vaccinia I3 promoter, synthetic early/late (sE/L) promoter, 7.5 promoter, HH promoter, 11K promoter, and Pi promoter. While the promoters typically will be constitutive promoters, inducible promoters also can be used in the inventive vectors. Such inducible systems allow regulation of gene expression.

A cell comprising the peptide, nucleic acid encoding the peptide, or vector also is provided herein. Suitable cells include prokaryotic and eukaryotic cells, e.g., mammalian cells, yeast, fungi, and bacteria (such as *E. coli*). The cell can be in vitro, as is useful for research or for production of the peptide, or the cell can be in vivo. The cell can be a peptide-pulsed antigen presenting cell. Suitable antigen presenting cells include, but are not limited to, dendritic cells, B lymphocytes, monocytes, macrophages, and the like.

The peptide, nucleic acid, vector, or cell can be isolated. The term "isolated" as used herein encompasses compounds or compositions that have been removed from a biological environment (e.g., a cell, tissue, culture medium, body fluid, etc.) or otherwise increased in purity to any degree (e.g., isolated from a synthesis medium). Isolated compounds and compositions, thus, can be synthetic or naturally produced.

The peptide, nucleic acid, vector, or cell can be formulated as a composition (e.g., pharmaceutical composition) comprising the peptide, nucleic acid, vector, or cell and a carrier (e.g., a pharmaceutically or physiologically acceptable carrier). Furthermore, the peptide, nucleic acid, vector, cell, or composition of the invention can be used in the methods described herein alone or as part of a pharmaceutical formulation.

The composition (e.g., pharmaceutical composition) can comprise more than one peptide, nucleic acid, vector, or cell or composition of the invention. Alternatively, or in addition, the composition can comprise one or more other pharmaceutically active agents or drugs. Examples of such other pharmaceutically active agents or drugs that may be suitable for use in the pharmaceutical composition include anticancer agents (e.g., chemotherapeutic drugs), antibiotics, antiviral drugs, antifungal drugs, cyclophosphamide, and combinations thereof. Suitable anticancer agents include, without limitation, alkylating agents, nitrogen mustards, folate antagonists, purine antagonists, pyrimidine antagonists, spindle poisons, topoisomerase inhibitors, apoptosis inducing agents, angiogenesis inhibitors, podophyllotoxins, nitrosoureas, cisplatin, carboplatin, interferon, asparginase, tamoxifen, leuprolide, flutamide, megestrol, mitomycin, bleomycin, doxorubicin, irinotecan, taxol, geldanamycin (e.g., 17-AAG), and various anti-cancer peptides and antibodies known in the art.

The carrier can be any of those conventionally used and is limited only by physio-chemical considerations, such as solubility and lack of reactivity with the active compound(s) and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular peptide, nucleic acid, vector, cell, or composition thereof of the invention and other active agents or drugs used, as well as by the particular method used to administer the peptide, nucleic acid, vector, cell, or composition thereof.

The composition additionally or alternatively can comprise one or more immunostimulatory/regulatory molecules. Any suitable immunostimulatory/regulatory molecule can be used, such as interleukin (IL)-2, IL-6, IL-12, interferon (IFN)-γ, tumor necrosis factor (TNF)-α, B7.1, B7.2, ICAM-1, LFA-3, CD70, RANTES, G-CSF, OX-40L, 41 BBL, anti-CTLA-4, and combinations thereof. Preferably, the composition comprises a combination of B7.1, ICAM-1, and LFA-3 (also referred to a TRICOM). The one or more immunostimulatory/regulatory molecules can be administered in the form of vector (e.g., a recombinant viral vector, such as a poxvirus vector) comprising a nucleic acid encoding one or more immunostimulatory/regulatory molecules. For example, the one or more immunostimulatory/regulatory molecules (e.g., IL-12) can be administered in the form of a DNA plasmid with or without chitosan. Alternatively, the one or more immunostimulatory/regulatory molecules can be administered as a protein (e.g., recombinant protein), such as a protein (e.g., recombinant IL-12) admixed with chitosan.

In one embodiment of the invention, the composition comprises a first recombinant poxvirus vector comprising the nucleic acid encoding the inventive peptide and second recombinant poxvirus vector comprising a nucleic acid encoding B7.1, ICAM-1, and LFA-3. In another embodiment, the nucleic acid encoding the inventive peptide and the nucleic acid encoding B7.1, ICAM-1, and LFA-3 are in the same recombinant poxvirus vector.

The invention provides a method of enhancing an immune response against a NGEP-expressing cancer (e.g., prostate cancer) in a host comprising administering a therapeutically effective amount of the peptide, nucleic acid, vector, cell, or composition thereof to the host, wherein the immune response in the host is enhanced. The inventive peptide, nucleic acid, vector, cell, or composition thereof can be used to prevent the development of a NGEP-expressing cancer (e.g., prostate cancer), particularly in an individual at higher risk to develop such cancer than other individuals, or to treat a patient afflicted with a NGEP-expressing cancer (e.g., prostate cancer). The inventive peptide, nucleic acid, vector, cell, or composition thereof can be used to treat a host with any stage NGEP-expressing cancer (e.g., stages I-IV of prostate cancer).

The peptide, nucleic acid, vector, cell, or composition thereof can be administered to the host by any method. For example, the peptide or nucleic acid encoding the peptide (e.g., as a vector) can be introduced into a cell (e.g., in a host) by any of various techniques, such as by contacting the cell with the peptide, the nucleic acid, or a composition comprising the nucleic acid as part of a construct, as described herein, that enables the delivery and expression of the nucleic acid. Specific protocols for introducing and expressing nucleic acids in cells are known in the art (see, e.g., Sambrook et al. (eds.), supra; and Ausubel et al., supra).

Suitable methods of administering peptides, nucleic acids, vectors, cells, and compositions to hosts are known in the art. The host can be any suitable host, such as a mammal (e.g., a rodent, such as a mouse, rat, hamster, or guinea pig, rabbit, cat, dog, pig, goat, cow, horse, primate, or human).

For example, the peptide, nucleic acid, or vector (e.g., recombinant poxvirus) can be administered to a host by exposure of tumor cells to the peptide, nucleic acid, or vector ex vivo or by injection of the peptide, nucleic acid, or vector into the host. The peptide, nucleic acid, vector (e.g., recombinant poxvirus) or combination of vectors, cell, and composition can be directly administered (e.g., locally administered) by direct injection into the cancerous lesion or tumor or by topical application (e.g., with a pharmaceutically acceptable carrier).

The peptide, nucleic acid, vector, cell, or composition thereof can be administered alone or in combination with adjuvants, incorporated into liposomes (as described in, e.g., U.S. Pat. Nos. 5,643,599, 5,464,630, 5,059,421, and 4,885,172), with cytokines, with biological response modifiers (e.g., interferon, interleukin-2 (IL-2), and colony-stimulating factors (CSF, GM-CSF, and G-CSF), or other reagents in the art that are known to enhance immune response.

Examples of suitable adjuvants include alum, aluminum salts, aluminum phosphate, aluminum hydroxide, aluminum silica, calcium phosphate, incomplete Freund's adjuvant, QS21, and RIBI DETOX™ adjuvant (an adjuvant comprising as active ingredients the cell skeleton from *Mycobacterium phlei* and monophosphoryl lipid A from Salmonella Minnesota R595 prepared as an oil-in-water emulsion with squalene and polysorbate 80).

A particularly preferred adjuvant for use in the invention is GM-CSF. GM-CSF has been shown to be an effective vaccine adjuvant because it enhances antigen processing and presentation by dendritic cells. Experimental and clinical studies suggest that recombinant GM-CSF can boost host immunity directed at a variety of immunogens.

GM-CSF can be administered using a viral vector (e.g., poxvirus vector) or as an isolated protein in a pharmaceutical formulation. GM-CSF can be administered to the host before, during, or after the initial administration of the peptide, nucleic acid, vector, cell, or composition thereof to enhance the antigen-specific immune response in the host. For example, recombinant GM-CSF protein can be administered to the host on each day of vaccination with the peptide, nucleic acid, vector, cell, or composition thereof and for each of the following 3 days (i.e. a total of 4 days). Any suitable dose of GM-CSF can be used. For instance, 50-500 µg (e.g., 100 µg, 200 µg, 300 µg, 400 µg, and ranges thereof) of recombinant GM-CSF can be administered per day. The GM-CSF can be administered by any suitable method (e.g., subcutaneously) and, preferably, is administered at or near the site of the vaccination of a host with the peptide, nucleic acid, vector, cell, or composition thereof.

In one embodiment, the inventive peptide can be conjugated to helper peptides or to large carrier molecules to enhance the immunogenicity of the peptide. These molecules include, but are not limited to, influenza peptide, tetanus toxoid, tetanus toxoid CD4 epitope, *Pseudomonas* exotoxin A, poly-L-lysine, a lipid tail, endoplasmic reticulum (ER) signal sequence, and the like.

The inventive peptide also can be conjugated to an immunoglobulin molecule using art-accepted methods. The immunoglobulin molecule can be specific for a surface receptor present on tumor cells, but absent or in very low amounts on normal cells. The immunoglobulin also can be specific for a specific tissue (e.g., prostate tissue). Such a peptide-immunoglobulin conjugate allows for targeting of the peptide to a specific tissue and/or cell.

The peptide, nucleic acid, vector, cell, or composition thereof is administered to a host (e.g., mammal, such as a human) in an amount effective to generate a NGEP-specific immune response, preferably a cellular immune response. The efficacy of the peptide, nucleic acid, vector, or cell as an immunogen may be determined by in vivo or in vitro parameters as are known in the art. These parameters include but are not limited to antigen specific cytotoxicity assays, regression of tumors expressing NGEP or NGEP epitopes, inhibition of cancer cells expressing NGEP or NGEP epitopes, production of cytokines, and the like.

Any suitable dose of the peptide, nucleic acid, vector, or cell or composition thereof can be administered to a host. The appropriate dose will vary depending upon such factors as the host's age, weight, height, sex, general medical condition, previous medical history, disease progression, and tumor burden and can be determined by a clinician. For example, the peptide can be administered in a dose of about 0.05 mg to about 10 mg (e.g., 0.1 mg, 0.5 mg, 1 mg, 2 mg, 3 mg, 4 mg, 5 mg, 6 mg, 7 mg, 8 mg, 9 mg, and ranges thereof) per vaccination of the host (e.g., mammal, such as a human), and preferably about 0.1 mg to about 5 mg per vaccination. Several doses (e.g., 1, 2, 3, 4, 5, 6, or more) can be provided (e.g., over a period of weeks or months). In one embodiment a dose is provided every month for 3 months.

When the vector is a viral vector, a suitable dose can include about $1\times10^5$ to about $1\times10^{12}$ (e.g., $1\times10^6$, $1\times10^7$, $1\times10^8$, $1\times10^9$, $1\times10^{10}$, $1\times10^{11}$, and ranges thereof) plaque forming units (pfus), although a lower or higher dose can be administered to a host. For example, about $2\times10^8$ pfus can be administered (e.g., in a volume of about 0.5 mL).

The inventive cells (e.g., cytotoxic T cells) can be administered to a host in a dose of between about $1\times10^5$ and $2\times10^{11}$ (e.g., $1\times10^6$, $1\times10^2$, $1\times10^8$, $1\times10^9$, $1\times10^{10}$, and ranges thereof) cells per infusion. The cells can be administered in, for example, one to three (e.g., two) infusions. In addition to the administration of the cells, the host can be administered a biological response modifier, such as interleukin 2 (IL-2). When the cells to be administered are cytotoxic T cells, the administration of the cytotoxic T cells can be followed by the administration of the peptide, nucleic acid, vector, or composition thereof in order to prime the cytotoxic T cells to further expand the T cell number in vivo.

The invention provides a method of generating peptide-specific cytotoxic T lymphocytes in vivo or in vitro by stimulation of lymphocytes with an effective amount of the inventive peptide, nucleic acid, or vector, alone or in combination with one or more immunostimulatory/regulatory molecules and/or adjuvant or in a liposome formulation. The lymphocytes can be lymphocytes from any suitable source, e.g., peripheral blood, tumor tissues, lymph nodes, and effusions, such as pleural fluid or ascites fluid.

The NGEP peptide specific cytotoxic T lymphocytes are immunoreactive with NGEP. Preferably, the cytotoxic T lymphocytes inhibit the occurrence of tumor cells and cancer and inhibit the growth of, or kill, tumor cells expressing NGEP or epitopes thereof. The cytotoxic T lymphocytes, in addition to being antigen specific, can be MHC class I restricted. In one embodiment, the cytotoxic T lymphocytes are MHC class I HLA-A2 restricted. The cytotoxic T lymphocytes preferably have a CD8+ phenotype.

In one embodiment, lymphocytes are removed from the host and stimulated ex vivo with the peptide, nucleic acid, vector, cell, or composition thereof to generate cytotoxic T lymphocytes. The cytotoxic T lymphocytes can be administered to the host in order to enhance an immune response to prostate cancer, thereby inhibiting the prostate cancer. Accordingly, the invention provides a method of inhibiting prostate cancer in a host comprising (a) obtaining lymphocytes (e.g., from the host), (b) stimulating the lymphocytes with the peptide, nucleic acid, vector, cell, or composition thereof to generate cytotoxic T lymphocytes, and (c) administering the cytotoxic T lymphocytes to the host, wherein the prostate cancer is inhibited.

In another embodiment, lymphocytes within the host are stimulated by administration to the host of the peptide, nucleic acid, vector, cell, or composition thereof to generate cytotoxic T lymphocytes, which cytotoxic T lymphocytes enhance an immune response to prostate cancer, thereby inhibiting the prostate cancer.

The invention includes a prime and boost protocol. In particular, the protocol includes an initial "prime" with a composition comprising one or more recombinant poxvirus vectors encoding the inventive peptide and optionally one or more immunostimulatory/regulatory molecules, followed by one or preferably multiple "boosts" with a composition containing the inventive peptide or one or more poxvirus vectors encoding the inventive peptide and optionally one or more immunostimulatory/regulatory molecules.

The initial priming vaccination can comprise one or more poxvirus vectors. In one embodiment, a single poxvirus vector is used for delivery of the inventive peptide and one or more immunostimulatory/regulatory molecules. In another embodiment, two or more poxvirus vectors comprise the priming vaccination, which are administered simultaneously in a single injection.

The boosting vaccinations also can comprise one or more poxvirus vectors. In one embodiment, a single poxvirus vector is used for delivery of the inventive peptide and the one or more immunostimulatory/regulatory molecules of the boosting vaccination. In another embodiment, two or more poxvirus vectors comprise the boosting vaccination, which are administered simultaneously in a single injection.

Different poxviruses can be used to provide a heterologous prime/boost protocol using poxvirus vectors carrying different sets of therapeutic molecules for inoculations at different time intervals. For example, in one heterologous prime/boost combination, a first orthopox vector composition is used to prime, and a second avipox vector composition is used to boost.

The schedule for administration of the poxvirus vectors typically involves repeated administration of the boosting vector. The boosting vector can be administered 1-3 times (e.g., 1, 2, or 3 times) at any suitable time period (e.g., every 2-4 weeks) for any suitable length of time (e.g., 6-12 weeks for a total of at least 5-15 boosting vaccinations). For example, a protocol can involve 3 administrations of vaccinia at a regular, e.g., monthly, intervals followed by multiple administrations of fowlpox at regular intervals, e.g., monthly. In a particular embodiment, the host receives one vaccination with the priming vector, followed every 2 weeks thereafter with the boosting vector for 6 boosts, followed by every 4 weeks thereafter with the boosting vector, and continuing with the boosting vector for a period of time dependent on disease progression.

The invention further provides a kit that has at least a first recombinant poxvirus that has incorporated into its genome or portion thereof a nucleic acid encoding the inventive peptide in a pharmaceutically acceptable carrier. The first recombinant poxvirus also can comprise one or more genes encoding one or more immunostimulatory/regulatory molecules. In addition to the first recombinant poxvirus, the kit can have a second recombinant poxvirus that comprises one or more genes encoding one or more immunostimulatory/regulatory molecules in a pharmaceutically acceptable carrier. The kit further provides containers, injection needles, and instructions on how to use the kit. In another embodiment, the kit further provides an adjuvant such as GM-CSF and/or instructions for use of a commercially available adjuvant with the kit components.

The peptide, nucleic acid, vector, cell, or composition thereof can be administered to a host by various routes including, but not limited to, subcutaneous, intramuscular, intradermal, intraperitoneal, intravenous, and intratumoral. When multiple administrations are given, the administrations can be at one or more sites in a host.

Administration of the peptide, nucleic acid, vector, cell, or composition thereof can be "prophylactic" or "therapeutic." When provided prophylactically, the peptide, nucleic acid, vector, cell, or composition thereof is provided in advance of tumor formation to allow the host's immune system to fight against a tumor that the host is susceptible of developing. For example, hosts with hereditary cancer susceptibility are a preferred group of patients treated with such prophylactic immunization. The prophylactic administration of the peptide, nucleic acid, vector, cell, or composition thereof prevents, ameliorates, or delays the NGEP-expressing cancer (e.g., prostate cancer). When provided therapeutically, the peptide, nucleic acid, vector, cell, or composition thereof is provided at or after the diagnosis of the NGEP-expressing cancer (e.g., prostate cancer).

When the host has already been diagnosed with the NGEP-expressing cancer (e.g., prostate cancer) or metastatic cancer, the peptide, nucleic acid, vector, cell, or composition thereof can be administered in conjunction with other therapeutic treatments such as chemotherapy or radiation.

In a preferred embodiment, the administration of the peptide, nucleic acid, vector, cell, or composition thereof to a host results in a host cell expressing the inventive peptide and optionally one or more immunostimulatory/regulatory molecules that were co-administered. The inventive peptide (i.e., NGEP antigen) can be expressed at the cell surface of the infected host cell. The one or more immunostimulatory/regulatory molecules can be expressed at the cell surface or may be actively secreted by the host cell. The expression of both the NGEP antigen and the immunostimulatory/regulatory molecule provides the necessary MHC restricted peptide to specific T cells and the appropriate signal to the T cells to aid in antigen recognition and proliferation or clonal expansion of antigen specific T cells. The overall result is an upregulation of the immune system. Preferably, the upregulation of the immune response is an increase in antigen specific T-helper lymphocytes and/or cytotoxic lymphocytes, which are able to kill or inhibit the growth of a prostate cancer cell.

There are a variety of suitable formulations of the pharmaceutical composition for the inventive methods. The following formulations for parenteral, subcutaneous, intravenous, intramuscular, and interperitoneal administration are exemplary and are in no way limiting. One skilled in the art will appreciate that these routes of administering the peptide, nucleic acid, vector, cell, or composition of the invention are known, and, although more than one route can be used to administer a particular compound, a particular route can provide a more immediate and more effective response than another route.

Injectable formulations are among those formulations that are preferred in accordance with the present invention. The requirements for effective pharmaceutical carriers for injectable compositions are well-known to those of ordinary skill in the art (see, e.g., Pharmaceutics and Pharmacy Practice, J.B. Lippincott Company, Philadelphia, Pa., Banker and Chalmers, eds., pages 238-250 (1982), and ASHP Handbook on Injectable Drugs, Toissel, 4th ed., pages 622-630 (1986)).

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The peptide, nucleic acid, vector, cell, or composition thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, and synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

The following examples further illustrate the invention but, of course, should not be construed as in any way limiting its scope.

EXAMPLE 1

This example demonstrates the determination of CTL epitopes of NGEP.

The primary amino acid sequence of human NGEP protein was analyzed for consensus motifs for HLA-A2 binding peptides. Seven 9-mer peptides and five 10-mer peptides were identified (see Table 1). NGEP peptides with a purity of greater than 95% were synthesized by American Peptide Inc. (Sunnyvale, Calif.). MUC-1 and CAP-7 peptides, which served as controls, were synthesized by Biosynthesis (Lewisville, Tex.) with a purity of greater than 95%.

Binding of the NGEP peptides to HLA-A2 molecules was evaluated by the regulation of HLA-A2 expression on T2 cells, as demonstrated by flow cytometry. The T2 cell-binding assay was repeated three times, and the results are set forth in Table 1. The T2 binding values are expressed in mean fluorescence intensity. The values in parentheses are fold increases as compared with the negative control (CAP-7 peptide).

TABLE 1

Binding of NGEP peptides to HLA-A2 molecules.

| Peptide* | Amino Acid Sequence | | NGEP Amino Acid Position | T2 Binding (fold increase) |
|---|---|---|---|---|
| P703 (L) | GLFDEYLEMV | (SEQ ID NO: 1) | 703-712 | 565 (6.4) |
| P215 (L) | VLLEVVPDV | (SEQ ID NO: 7) | 215-223 | 464 (5.2) |
| P113 (S) | LVWEEDLKL | (SEQ ID NO: 2) | 113-121 | 367 (4.1) |
| P356 (L) | WLLPAAVVGT | (SEQ ID NO: 3) | 356-365 | 354 (4.0) |

TABLE 1-continued

Binding of NGEP peptides to HLA-A2 molecules.

| Peptide* | Amino Acid Sequence | | NGEP Amino Acid Position | T2 Binding (fold increase) |
|---|---|---|---|---|
| P258 (L) | ILFEILAKT | (SEQ ID NO: 8) | 258-266 | 280 (3.1) |
| P10 (S) | GLGGPPLPTL | (SEQ ID NO: 4) | 10-19 | 212 (2.4) |
| P855 (L) | IVFEHVVFSV | (SEQ ID NO: 5) | 855-864 | 203 (2.3) |
| P143 (S) | FLDNIRAAGL | (SEQ ID NO: 6) | 143-152 | 203 (2.3) |
| P170 (L) | ALLSASWAV | (SEQ ID NO: 9) | 170-178 | 185 (2.1) |
| P557 (L) | ILILSKIYV | (SEQ ID NO: 10) | 557-565 | 162 (1.8) |
| P427 (L) | SLFMALWAV | (SEQ ID NO: 11) | 427-435 | 153 (1.7) |
| P846 (L) | LLAIRLWAV | (SEQ ID NO: 12) | 846-854 | 126 (1.4) |
| MUC-1 (P1240) | SLSYTNPAV | (SEQ ID NO: 13) | Positive control | 452 (5.1) |
| CAP-7 | HLFGYSWYK | (SEQ ID NO: 14) | Negative control | 88.0 |

*Peptides were used at a concentration of 25 µg/mL.
(L) = NGEP long form
(S) = NGEP short form
MUC-1 peptide is an HLA-A2-binding peptide.
CAP-7 peptide is an HLA-A3-binding CEA peptide The P703 peptide demonstrated the greatest efficiency for binding to the HLA-A2 molecule (6.4-fold higher than the negative control), though other peptides also demonstrated high levels of binding.

To determine the stability of peptide-MHC complexes, several of the identified peptides (at concentrations of 25 µg/mL) were incubated with T2 cells overnight. Unbound peptides were washed off, and delivery of new class 1 molecules to the cell surface was blocked by the addition of brefeldin A. Cells then were analyzed for the presence of peptide-HLA-A2 complexes at various time points, as indicated by the degree of mean fluorescence intensity. Of the peptides tested, the P703-HLA-A2 complexes demonstrated the most stable complexes (see FIG. 1A). P703 peptide also was determined to bind T2 cells at higher levels at various peptide concentrations than the P215 peptide and the positive control (see FIG. 1B).

To determine the immunogenicity of the inventive peptides, the ability to induce specific CTL in vitro was evaluated. T cell lines were generated against the P703 and P215 peptides using peripheral blood mononuclear cells (PBMC) of a patient with locally recurrent prostate cancer (patient A). The T cell lines generated using the P703 and P215 peptides were designated as T-A-P703 and T-A-P215, respectively. To evaluate the specificity of these T-cell lines, an IFN-γ release assay was performed using irradiated, autologous dendritic cells (DC) pulsed with the corresponding NGEP and control peptides (see FIG. 1C). The T-A-P703 cell line produced higher levels of IFN-γ compared to the T-A-P215 cell line. No IFN-γ was produced employing a control HIV gag peptide.

It has previously been demonstrated that peptide-specific T cells produce high levels of the chemokine lymphotactin after stimulation with agonist peptides. The T-A-P703 cell line produced higher levels of lymphotactin than the T-A-P215 cell line when stimulated with autologous DC pulsed with various concentrations of each corresponding peptide (see FIG. 1D).

EXAMPLE 2

This example demonstrates the ability of the inventive peptides to inhibit prostate cancer cells.

A T cell line was established from PBMC of a patient with metastatic prostate cancer (patient B) using the P703 peptide, which cell line was thus designated as T-B-P703. Similar to T-A-P703, T-B-P703 produced high levels of IFN-γ (876.5 pg/mL) in response to peptide-specific stimulation and undetectable levels of IFN-γ using the control HIV gag peptide.

To investigate the frequency of NGEP-specific CD8⁺ T cells in both the T-A-P703 and T-B-P703 cell lines, a NGEP-specific P703/HLA-A*0201 tetramer and anti-CD8 antibodies were used. As shown in FIGS. 2A-B, a higher frequency of NGEP-specific CD8⁺ T cells was generated in the T-A-P703 T-cell line (95.2%).

Both cell lines then were tested for cytotoxic activity against peptide-pulsed HLA-A2⁺ targets in a 6 hour CTL assay (see FIG. 2C). The T-A-P703 cell line specifically lysed C1RA2 cells pulsed with the P703 peptide at various effector: target (E:T) cell ratios with higher efficiency than the T-B-P703 cell line.

To determine if these T cell lines, raised against the P703 peptide, could kill target cells endogenously expressing full-length processed NGEP-L, a CTL assay was performed using MCF-7 tumor cells transfected with the NGEP-L gene (HLA-A2⁺, NGEP⁺) and untransfected MCF-7 cells (HLA-A2⁺, NGEP⁻) as a negative control (see FIG. 2D). The results showed that the T-A-P703 cells can specifically kill tumor cells endogenously expressing the NGEP-L gene.

EXAMPLE 3

This example demonstrates the immunogenicity of NGEP in prostate cancer patients.

To determine if prostate cancer patients recognized the NGEP-P703 epitope, PBMC from four patients with metastatic prostate cancer and from four healthy donors were analyzed for the presence of CD8+ T cells reactive with the NGEP-P703 tetramer. T cells (5×10⁵) were stained with 10 µl of PE-labeled NGEP-P703/HLA-A*0201 tetramer and anti-CD8 antibody. Tetramer PE-labeled HIV gag (SLYNTVATL (SEQ ID NO: 15))/HLA-A*0201 was used as a negative control. The results (expressed in percent of tetramer positive cells in PBMC) are set forth in Table 2.

Three of the four patients with metastatic prostate cancer (i.e., Patients 2, 3, and 4) had a higher frequency of NGEP-P703 specific CD8+ T cells as compared to the healthy donors (see Table 2).

These same four prostate cancer patients then were analyzed for tetramer binding after receiving six monthly cycles of a PSA-based vaccine (PSA/TRICOM). PBMC from all four patients showed higher tetramer binding post-vaccination as compared to pre-vaccination (see Table 2).

TABLE 2

Identification of NGEP-specific CD8+ T cells in healthy donors and prostate cancer patients using NGEP-P703/HLA-A* 0201 tetramer.

| Samples | NGEP-tetramer | HIV-tetramer |
|---|---|---|
| Healthy Donor | | |
| I | 0.49 | 0.20 |
| II | 0.88 | 0.25 |
| III | 0.89 | 0.41 |
| IV | 0.71 | 0.27 |
| Prostate Cancer Patients Pre-Vaccination | | |
| Patient 1 | 0.85 | 0.58 |
| Patient 2 | 1.77 | 0.16 |
| Patient 3 | 2.04 | 0.29 |
| Patient 4 | 1.52 | 0.52 |
| Prostate Cancer Patients Post-Vaccination | | |
| Patient 1 | 1.08 | 0.11 |
| Patient 2 | 2.70 | 0.30 |
| Patient 3 | 2.47 | 0.35 |
| Patient 4 | 3.42 | 0.82 |

These results provide evidence of cross-presentation of the NGEP epitope as a result of the vaccine therapy and provide further evidence of the immunogenicity of NGEP in prostate cancer patients.

An additional four patients with metastatic prostate cancer were analyzed pre- and post-vaccination with PSA/TRICOM for the generation of PSA-specific and NGEP-specific T cells in PBMC employing an ELISPOT assay for IFN production. All four patients were negative for PSA-specific T cells prior to vaccination with increases in PSA-specific T cells in three of four patients post-vaccination (see Table 3).

TABLE 3

Precursor frequency of T cells specific for PSA and NGEP peptides from peripheral blood of prostate cancer patients before (Pre) and after 6 cycles PSA/TRICOM (D167) vaccination.

| Patient | | PSA3a | NGEP P703 |
|---|---|---|---|
| Patient 5 | Pre | <1/200,000 | <1/200,000 |
| | D167 | 1/46,154 | 1/24,000 |
| Patient 6 | Pre | <1/200,000 | 1/150,000 |
| | D167 | 1/150,000 | 1/75,000 |

TABLE 3-continued

Precursor frequency of T cells specific for PSA and NGEP peptides from peripheral blood of prostate cancer patients before (Pre) and after 6 cycles PSA/TRICOM (D167) vaccination.

| Patient | | PSA3a | NGEP P703 |
|---|---|---|---|
| Patient 7 | Pre | <1/200,000 | <1/200,000 |
| | D167 | 1/75,000 | 1/31,579 |
| Patient 8 | Pre | <1/200,000 | <1/200,000 |
| | D167 | <1/200,000 | <1/200,000 |

Interestingly, the three patients demonstrating increases in PSA-specific T cells (i.e., Patients 5, 6, and 7) also showed increases in NGEP-specific T cells. Taken together (see Tables 2 and 3), these studies demonstrate the immunogenicity of NGEP in six of eight prostate cancer patients (i.e., Patients 2, 3, 4, 5, 6, and 7).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An immunogenic epitope having no more than 20 amino acid residues and comprising GLFDEYLEMV (SEQ ID NO:1), wherein the immunogenic epitope binds to HLA-A2.

2. The immunogenic epitope of claim 1, wherein the epitope consists of SEQ ID NO: 1.

3. A recombinant nucleic acid encoding the immunogenic epitope of claim 1, wherein the nucleic acid is operatively linked to a nucleic acid sequence capable of directing expression of the immunogenic epitope.

4. A vector comprising the nucleic acid of claim 3.

5. The vector of claim 4, wherein the vector is selected from the group consisting of a plasmid, yeast, poxvirus, retrovirus, adenovirus, herpes virus, polio virus, alphavirus, baculorvirus, and Sindbis virus.

6. The vector of claim 5, wherein the vector is a poxvirus selected from the group consisting of orthopox, vaccinia, avipox, fowlpox, capripox, and suipox.

7. An isolated cell comprising the immunogenic epitope of claim 1.

8. The cell of claim 7, wherein the cell is human.

9. The cell of claim 7, wherein the cell is an antigen presenting cell or tumor cell.

10. A composition comprising: (a) the immunogenic epitope of claim 1, and (b) a pharmaceutically acceptable carrier.

11. The composition of claim 10, further comprising an immunostimulatory/regulatory molecule.

12. The composition of claim 11, wherein the immunostimulatory/regulatory molecule is selected from the group consisting of interleukin (IL)-2, IL-6, IL-12, interferon (IFN)-γ, tumor necrosis factor (TNF)-α, B7.1, B7.2, ICAM-1, LFA-3, CD70, RANTES, G-CSF, OX-40L, 41 BBL, anti-CTLA-4 antibody, and combinations thereof.

13. The composition of claim 11, wherein the immunostimulatory/regulatory molecule is selected from the group consisting of (i) a plasmid encoding IL-12 complexed with chitosan and (ii) recombinant IL-12 admixed with chitosan.

14. The composition of claim 10, further comprising a chemotherapeutic drug, antibiotic, antiviral drug, antifungal drug, cyclophosphamide, or a combination thereof.

15. The composition of claim 10, further comprising an adjuvant.

16. The composition of claim 15, wherein the adjuvant is selected from the group consisting of alum, aluminum salts, aluminum phosphate, aluminum hydroxide, aluminum silica, calcium phosphate, incomplete Freund's adjuvant, QS21, and an adjuvant comprising as active ingredients the cell skeleton from *Mycobacterium phlei* and monophosphoryl lipid A from Salmonella Minnesota R595 prepared as an oil-in-water emulsion with squalene and polysorbate 80.

17. The composition of claim 15, wherein the adjuvant is granulocyte monocyte colony stimulating factor (GM-CSF).

18. The composition of claim 10, further comprising liposomes.

19. A method of enhancing an immune response against New Gene Expressed in Prostate (NGEP-L)-expressing prostate cancer cells in a host comprising administering a therapeutically effective amount of the composition of claim 15 to the host, wherein the immune response against NGEP-L-expressing prostate cancer cells in the host is enhanced.

20. A method of inhibiting New Gene Expressed in Prostate (NGEP-L)-expressing prostate cancer cells in a host comprising: (a) obtaining lymphocytes from the host, (b) stimulating the lymphocytes with an antigen presenting cell pulsed with the immunogenic epitope of claim 1 to generate cytotoxic T lymphocytes; and (c) contacting the host with the cytotoxic T lymphocytes, wherein the NGEP-L-expressing prostate cancer cells in the host are inhibited.

21. An isolated cell comprising the nucleic acid of claim 3.

22. A composition comprising:
(a) the nucleic acid of claim 3, and
(b) a pharmaceutically acceptable carrier.

23. An isolated cell comprising the vector of claim 4.

24. A composition comprising:
(a) the vector of claim 4, and
(b) a pharmaceutically acceptable carrier.

\* \* \* \* \*

SEQUENCE LISTING

<160> NUMBER OF SEQ ID NOS: 15

<210> SEQ ID NO 1
<211> LENGTH: 10

```
<212> TYPE: PRT
<213> ORGANISM: Artificial Sequence
<220> FEATURE:
<223> OTHER INFORMATION: Synthetic

<400> SEQUENCE: 1

Gly Leu Phe Asp Glu Tyr Leu Glu Met Val
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Leu Val Trp Glu Glu Asp Leu Lys Leu
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Trp Leu Leu Pro Ala Ala Val Val Gly Thr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

Gly Leu Gly Gly Pro Pro Leu Pro Thr Leu
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic

<400> SEQUENCE: 5

Ile Val Phe Glu His Val Val Phe Ser Val
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Phe Leu Asp Asn Ile Arg Ala Ala Gly Leu
1               5                   10

<210> SEQ ID NO 7
<211> LENGTH: 9
<212> TYPE: PRT
<213> ORGANISM: Artificial Sequence
```

```
<220> FEATURE:
<223> OTHER INFORMATION: Synthetic

<400> SEQUENCE: 7

Val Leu Leu Glu Val Val Pro Asp Val
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Ile Leu Phe Glu Ile Leu Ala Lys Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Ala Leu Leu Ser Ala Ser Trp Ala Val
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic

<400> SEQUENCE: 10

Ile Leu Ile Leu Ser Lys Ile Tyr Val
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic

<400> SEQUENCE: 11

Ser Leu Phe Met Ala Leu Trp Ala Val
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Leu Leu Ala Ile Arg Leu Trp Ala Val
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic
```

```
<400> SEQUENCE: 13

Ser Leu Ser Tyr Thr Asn Pro Ala Val
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

His Leu Phe Gly Tyr Ser Trp Tyr Lys
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

Ser Leu Tyr Asn Thr Val Ala Thr Leu
1               5
```